United States Patent [19]

Hussmann

[11] Patent Number: 4,898,982
[45] Date of Patent: Feb. 6, 1990

[54] PREPARATION OF DIARYL ETHERS AND DIARYL SULFIDES

[75] Inventor: Gregory P. Hussmann, Batavia, Ill.

[73] Assignee: Amoco Corporation, Chicago, Ill.

[21] Appl. No.: 121,151

[22] Filed: Nov. 16, 1987

[51] Int. Cl.$^4$ .................. C07C 148/00; C07C 43/275
[52] U.S. Cl. ..................................... 568/58; 568/632; 568/635
[58] Field of Search .................. 568/58, 632, 635; 502/240

[56] References Cited

U.S. PATENT DOCUMENTS

| | | | |
|---|---|---|---|
| 2,436,125 | 2/1948 | Spence | 502/240 |
| 4,085,143 | 4/1978 | Holmes | 502/240 |
| 4,465,889 | 8/1984 | Anthony et al. | 502/240 |

FOREIGN PATENT DOCUMENTS

| | | | |
|---|---|---|---|
| 495143 | 11/1938 | United Kingdom | 502/240 |
| 911246 | 11/1962 | United Kingdom | |

OTHER PUBLICATIONS

S. Karuppannasamy et al., J. Catalysis 63, 433–437 (1980), Reactions of Phenols and Alcohols over Thoria.
E. Briner et al., Heb. Chin. Acta., vol. 15, Aug. 1932, pp. 1234–1241, Catalytic Dehydration of Phenols (English translation).
S. Karuppannasamy et al., Proc. Nat'l. Symp. Catal., 4th, 1978, p. 443, Investigations of Phenol Decomposition on Thoria Catalysts.
S. Karuppanasamy et al., J. Catalysis, 66, 281–289 (1980), Reactions of Phenols and Alcohols over Thoria: Mechanism of Ether Formation.
Abstract of Japanese Patent 84-315126, published Nov. 8, 1984.
Sabatier et al., Comptes rendus, vol. 151, 1910, pp. 492–494.
Sabatier et al., Comptes rendus, vol. 155, 1912, pp. 260–262.

Primary Examiner—Mary E. Ceperley
Attorney, Agent, or Firm—James R. Henes; William H. Magidson; Ralph C. Medhurst

[57] ABSTRACT

A method is disclosed for the preparation of diaryl ethers and diaryl sulfides by heating a phenol, a thiophenol, a β-hydroxy-substituted fused aromatic ring-system compound or a β-thio-substituted fused aromatic ring-system compound in the presence of thoria deposited on a neutral support.

14 Claims, No Drawings

PREPARATION OF DIARYL ETHERS AND DIARYL SULFIDES

BACKGROUND OF THE INVENTION

1. Field of the Invention

This invention relates generally to the preparation of diaryl ethers or diaryl sulfides by a process involving a thoria-containing catalyst and more particularly concerns the use in such process of a catalyst comprising thoria deposited on neutral support particles.

2. Description of the Prior Art

The commercial importance of diphenyl ether-based monomers and diphenyl sulfide-based monomers in engineering polymer formulations is well recognized. Either such materials are themselves potential useful monomers or can serve as precursors to monomers of proven utility such as oxybisanaline. For example, 4,4'-diaminodiphenyl ether is currently used in the preparation of Torlon® and of Vespel®. Other diphenyl ether-based monomers which are of potential commercial importance include diacids, diols or dianhydrides of diphenyl ether. Although diphenyl ether-based monomers and diphenyl sulfide-based monomers have proven utility, their high cost and the lack of a convenient method of preparation have hindered any large volume applications of such monomers.

A potentially inexpensive method of preparing diphenyl ether-based monomers and diphenyl sulfide-based monomers is the catalyzed dehydrative coupling of phenols or thiophenols, respectively. Unsupported and supported thorias have been employed as catalysts in the dehydrative coupling of phenols or thiophenols to form the corresponding diphenyl ethers of diphenyl sulfides, respectively. For example, British Patent Specification No. 911,246 discloses a method for the dehydrative coupling of a phenol to the corresponding diphenyl oxide in the presence of a catalyst containing thoria supported on alpha alumina, preferably in the vapor phase, and at substantially atmospheric pressure and at a temperature between 300° C. and 550° C., for example, 475° C. The catalyst was prepared by impregnating alumina with thorium nitrate tetrahydrate and then decomposing the thorium nitrate to form thorium oxide. The patent states that, under conditions conducive to high catalyst activity in the dehydrative coupling reaction, the activity of the catalyst disclosed therein decreased with use. Furthermore, the data in the patent illustrates that the coupling reaction did not take place stereospecifically.

Karuppannasamy et al., "Investigations of Phenol Decomposition on Thoria Catalysts," in Proc. Natl. Symp. Catal., 4th, 1978, pp. 443-450, and "Reactions of Phenols and Alcohols over Thoria," in Journal of Catalysts, Vol. 63, pp. 433-437 (1980), reported on studies of the dehydrative coupling of phenols in the presence of a thoria catalyst that was prepared by a procedure involving precipitation from a thorium nitrate solution by addition thereto of ammonia. The article contains no mention of a catalyst support and evidently the thoria catalyst was unsupported. The authors also indicated that thoria catalysts can also be prepared by the thermal decomposition of thorium nitrate and thorium oxalate. In the article in the Journal of Catalysts, the authors indicated that the results on catalysts prepared by these three different routes were comparable qualitatively.

Karuppannasamy et al., "Reactions of Phenols and Alcohols over Thoria: Mechanism of Ether Formation," Journal of Catalysts, Vol. 66, pp. 281-289 (1980) reported on the dehydrative coupling of phenols in the presence of a thoria catalyst that was prepared by a procedure involving the thermal decomposition of thorium oxalate. The article contains no mention of a catalyst support, and evidently the thoria catalyst was unsupported. The authors also indicated that thoria catalysts can also be prepared by the thermal decomposition of thorium nitrate or the calcination of thorium hydroxide and that the results on catalysts prepared by these three different routes were qualitatively similar.

Briner and Bron, "Catalytic Dehydration of Phenols; Influence and Nature of the Position of Substituted Groups," Heb. Chin. Acta., Vol. 15, pp. 1234-1241 (Aug. 1932) disclose the use in the aforesaid dehydrative coupling of phenols of a thoria catalyst. The method of preparation of the catalyst was not disclosed.

Sabatier et al., Computes Rendies, 1912, p. 260 and 1914, p. 608 disclose the use of unsupported thoria to catalyze the dehydrative coupling of phenols.

However, the selectivity of such thoria catalysts for the production of certain, highly desirable stereospecific substituted diaryl ethers and diaryl sulfides is often less than is generally acceptable for a commercial process. Furthermore, as disclosed in British Patent Specification No. 911,246, upon use under the conditions generally employed in the dehydrative coupling of phenols, thoria catalysts typically experience a significant loss of activity for such coupling reactions, with a further reduction in their selectivity for the production of certain, highly desirable stereospecific substituted diaryl ethers.

OBJECTS OF THE INVENTION

It is therefore a general object of the present invention to provide an improved process for the catalytic dehydrative coupling of phenols, thiophenols, β-hydroxy-substituted fused aromatic ring-system compounds, or β-thio-substituted fused aromatic ring-system compounds having improved selectivity for the production of certain stereospecific substituted diaryl ethers and substituted diaryl sulfides.

It is another object of the present invention to provide an improved process for the catalytic dehydrative coupling of phenols, thiophenols, β-hydroxy-substituted fused aromatic ring-system compounds, or β-thio- substituted fused aromatic ring-system compounds having an improved catalytic activity for such reaction.

Other objects and advantages of the present invention will become apparent upon reading the following detailed description and appended claims.

SUMMARY OF THE INVENTION

These objects are achieved by an improved method for the formation of a diaryl ether or a diaryl sulfide comprising heating a phenol, thiophenol, a β-hydroxy-substituted fused aromatic ring-system compound, or a β-thio-substituted fused aromatic ring-system compound in the gas phase at a temperature in the range of from about 300° C. to about 600° C. in the presence of a bed of catalyst particles comprising thoria deposited on a neutral support.

DETAILED DESCRIPTION OF THE PREFERRED EMBODIMENTS

Reactants that are suitable for use in the method of this invention are either a phenol, a thiophenol, a β- hydroxy-substituted fused aromatic ring-system compound, or a β-thio-substituted fused aromatic ring-system compound which, apart from the phenolic hydroxy or thio substituent in each thereof, is either otherwise unsubstituted or substituted either with at least one alkyl group containing from 1 to 10 carbon atoms, preferably from 1 to 3 carbon atoms, or with at least one other substituent that is inert to the dehydrative coupling reaction, or with both thereof. Each of the aforesaid optional alkyl substituent and other inert substituent is attached to an aromatic ring carbon atom that is attached to at least one aromatic ring carbon atom that is located other than ortho to the phenolic hydroxy or thio substituent. Optionally, an aforesaid optional alkyl group substituent contains 3 or 4 carbon atoms and, in combination with an aromatic ring of the phenol, thiophenol or fused aromatic ring-system compound, forms a saturated ring fused to such aromatic ring. Preferably the reactant is a phenol or a β-hydroxy-substituted fused aromatic ring-system compound.

Therefore, suitable such materials (with the products formed therefrom by the method of this invention indicated in parenthesis) include the following: phenol (diphenyl ether), β-naphthol (dinaphthyl ether), m-cresol (3,3′-dimethyldiphenyl ether), p-cresol (4,4′-dimethyldiphenyl ether), 3,4-xylenol (3,3′,4,4′-tetramethyldiphenyl ether), 3,5-xylenol (3,3′,5,5′-tetramethyldiphenyl ether), 3,4,5-trimethylphenol (3,3′,4,4′,5,5′-hexamethyldiphenyl ether), 5-tetralinol (ditetralin ethers), and mixtures thereof such as m- and p-cresol (3,4′-dimethyldiphenyl ether). In addition, suitable feedstocks include compounds corresponding to the above-mentioned except that one or more methyl substituents therein are replaced by an ethyl or phenyl substituent, and/or the hydroxy substituent is replaced by a thio substituent.

A catalyst suitable for use in the method of this invention comprises thoria deposited on a neutral support. In this context, a neutral support has no or very weak acidic or basic properties. Suitable neutral supports include pure silica, pure zirconia, carbon, asbestos, and quartz. In the present context, the term "pure" means that the silica or zirconia contains less than 1000, preferably less than 500, parts per million of metallic impurities, calculated as the elemental metals. Preferably the support is fumed silica or fumed zirconia. In this context, "fumed" refers to the well-known method commonly used to prepare silica or zirconia. Fumed silica and fumed zirconia are commercially available for example, from the G. L. Cabot Company.

The thoria content of the catalyst employed in the method of this invention is in the range of from about 1, preferably from about 10, to about 70 preferably to about 50 weight percent, calculated as $ThO_2$ and based on the weight of the catalyst.

Preferably, the catalyst is prepared by direct calcination at 600° C.–800° C. of a suitable thorium salt impregnated by any convenient, conventional technique on the neutral support. Calcination at temperatures outside this range afforded catalysts of significantly lower activity. Preferably, the support is calcined at 500° C.–1000° C. prior to being impregnated with the thorium salt. The aforesaid suitable thorium salt is typically impregnated on the neutral support by the incipient wetness method. Suitable thorium salts include the nitrate (tetrahydrate), carbonate, oxalate and hydroxide.

In practice, the method of this invention is performed by passing the phenol, thiophenol, β-hydroxy-substituted fused aromatic ring system compound or β-thio-substituted fused aromatic ring system compound in the vapor phase through a bed of particles of the aforesaid catalyst at a weight hourly space velocity in the range of from about 0.01 preferably from about 0.1 to about 100, preferably to about 20, more preferably to about 5 grams of the feed compound per gram of the catalyst per hour. Preferably, a solvent such as benzene, toluene, a xylene, a hexane, a heptane, tetrahydrofuran or 1,4-dioxane is used.

Preferably, the aforesaid phenol, thiophenol, β-hydroxy-substituted fused aromatic ring-system compound, or β-thio-substituted fused aromatic ring-system compound is passed through the bed of aforesaid catalyst particles in the presence of a diluent gas which is substantially inert under the conditions employed in the method of this invention and which serves as a carrier gas to sweep the phenol, thiophenol, or β-hydroxy-substituted fused aromatic ring-system compound or β-thio-substituted fused aromatic ring-system compound through the catalyst bed. Suitable materials for this purpose include nitrogen, hydrogen and argon. Preferably, hydrogen is employed. The use of hydrogen affords the additional advantage of increasing catalyst lifetime.

The method of this invention is performed at a temperature in the range of from about 300° C., preferably from about 400° C., to about 600° C., preferably to about 500° C. At reaction temperatures below 300° C., little or no conversion of the reactant occurred. At reaction temperatures above 600° C. the formation of by-products was enhanced, and selectivity for the formation of the desired product rapidly decreased. At any given reaction temperature within the aforesaid range the catalyst undergoes deactivation on a long term basis, for example, losing about 38 percent of its initial activity over 10 days of operation. However, this deactivation can be overcome by a programmed increase in reaction temperature. Thus, it is highly preferred that, in the practice of the method of this invention, the reaction temperature is gradually increased within the temperature range of from about 400° C., preferably from about 425° C., to about 500° C., preferably to about 450° C., at a rate of increase that is from about 0.04° C. per day to about 0.45° C. per day, preferably to about 0.2° C. per day, more preferably to about 0.085° C. per day. Such temperature increase during the practice of the method of this invention affords the benefits of maintaining catalyst activity and yield of the desired product substantially constant.

The method of this invention is performed at a pressure of from about 0.1 atmosphere, preferably from about 1 atmosphere to about 50 atmosphere, preferably to about 5 atmosphere.

The present invention will be more clearly understood from the following specific examples.

EXAMPLE 1

8.3 grams of 14/40-mesh particles of a neutral, fumed silica (Cabosil-L90D from J. L. Cabot Co.,) (which had been mixed as a powder with water to form a thick paste which was then dried overnight at 100° C. and then calcined at 500° C.–1000° C. for 12 hours and finally sieved) having a pore volume of 2.4 cubic centimeters per gram, as measured by water adsorption, were immersed for 20 minutes in 33.5 grams of a stirred aqueous solution of $Th(NO_3)_4 \cdot 4H_2O$ at a concentration of 40 weight percent. The resulting particles impregnated with $Th(NO_3)_2 \cdot 4H_2O$ were then dried overnight at 110° C. and then calcined at 650° C. for 12 hours. The resulting catalyst particles contained 44 weight percent of thoria, calculated as $ThO_2$ and based on the total weight of the impregnated catalyst particles.

EXAMPLE 2

The procedure of Example 1 was repeated, except that a neutral, fumed silica particle (Cabosil M-5 from J. L. Cabot Co.) (which had been mixed as a powder with water to form a thick paste which was then dried overnight at 100° C. and then calcined at 500° C.–1000° C. for 12 hours and finally sieved) having a pore volume of 2.0 cubic centimeters per gram, as measured by water absorption, and being at least 99.99 weight percent pure and containing less than 2 parts per million by weight of aluminum and less than 5 percent per million by weight sodium, was employed instead of the fumed silica employed in Example 1. The resulting catalyst particles contained 42 weight percent of thoria, calculated as $ThO_2$ and based on the total weight of the impregnated catalyst particles.

EXAMPLE 3

The procedure of Example 2 was repeated, except that a 28 weight percent concentration solution of $Th(NO_3)_4 \cdot 4H_2O$ was employed instead of the solution containing 40 weight percent of $Th(NO_3)_2 \cdot 4H_2O$ employed in Example 2. The resulting catalyst particles contained 27 weight percent of thoria, calculated as $ThO_2$ and based on the total weight of the impregnated catalyst particles.

EXAMPLE 4

The procedure of Example 1 was repeated, except that 10 grams of 14/40-mesh acidic, relatively lower purity, (containing 300 parts per million by weight of aluminum and 800 parts per million by weight of sodium) colloidal silica particles (from Ludox Company) (which had been mixed as a powder with water to form a thick paste which was then dried overnight at 100° C. and then calcined at 500° –1000° C. for 12 hours and finally seived) containing 0.04 weight percent of alumina and having a pore volume of 1.5 cubic centimeters per gram, as measured by water adsorption, were used, instead of the fumed silica particles employed therein. The resulting catalyst particles contained 23 weight percent of thoria, calculated as $ThO_2$ and based on the total weight of the impregnated catalyst particles.

EXAMPLE 5

The procedure of Example 1 was repeated, except that 10 grams of 14/40-mesh, acidic, relatively lower purity, (only 99 weight percent pure and containing 1000 parts per million by weight of aluminum and 60 parts per million by weight of sodium) silicalite particles (which had been mixed as a powder with water to form a thick paste which was then dried overnight at 100° C. and then calcined at 500° –1000° C. for 12 hours and finally sieved) having a pore volume of 0.5 cubic centimeter per gram, as measured by water adsorption, were used instead of the fumed silica employed therein. The resulting catalyst particles contained 17 weight percent of thoria, calculated as $ThO_2$ and based on the total weight of impregnated catalyst particles.

EXAMPLE 6

The procedure of Example 1 was repeated, except that 10 grams of 14/40-mesh neutral, zirconia particles (at 99.99 weight percent purity, containing less than 5 parts per million by weight of aluminum, silicon and sodium combined) (from Alrich Corporation) (which had been mixed as a powder with water to form a thick paste which was then dried overnight at 100° C. and then calcined at 500° –1000° C. for 12 hours and finally sieved) having a pore volume of 0.5 cubic centimeter per gram, as measured by water adsorption, were used, instead of the fumed silica particles employed therein. The resulting catalyst particles contained 16 weight percent of thoria, calculated as $ThO_2$ and based on the total weight of the impregnated catalyst particles.

EXAMPLE 7

The procedure of Example 1 was repeated, except that 21.2 grams of an aqueous solution containing 50 weight percent of $Th(NO_3)_4 \cdot 4H_2O$ and 27.7 grams of 14/42-mesh titanium oxide particles (at 99.5 weight percent purity, containing less than 0.3 weight percent of alumina) (P-25 from Degussa Corporation) (which had been mixed with water to form a thick paste which was then dried overnight at 100° C. and then calcined at 500° C.–1000° C. for 12 hours) having a pore volume of 0.389 cubic centimeter per gram, as measured by water adsorption, were used instead of the solution and fumed silica particles employed therein. The resulting catalyst particles contained 15 weight percent of thoria, calculated as $ThO_2$ and based on the total weight of the impregnated catalyst particles.

EXAMPLE 8

The procedure of Example 1 was repeated, except that 8.67 grams of an aqueous solution containing 54 weight percent of $Th(NO_3)_4 \cdot 4H_2O$ and 10.7 grams of 14/42-mesh basic magnesium oxide particles (at 98 weight percent purity, from Alpha Company) (which had been mixed with water to form a thick paste which was then dried overnight at 100° C. and then calcined at 500° C.–1000° C. for 12 hours) having a pore volume of 0.343 cubic centimeter per gram, as measured by water adsorption, were used, instead of the solution and fumed silica particles employed therein. The resulting catalyst particles contained 17 weight percent of thoria, calculated as $ThO_2$ and based on the total weight of the impregnated catalyst particles.

EXAMPLE 9

The procedure of Example 1 was repeated, except that 14.95 grams of an aqueous solution containing 50 weight percent of the $Th(NO_3)_4 \cdot 4H_2O$ and 10.0 grams of 14/42-mesh fumed, acidic alumina particles (at about 99.6 weight percent purity, from Degussa) (which had been mixed with water to form a thick paste which was then dried overnight at 100° C. and then calcined at 500° C.–1000° C. for 12 hours) having a pore volume of 0.68 cubic centimeter per gram, as measured by water adsorption, were used, instead of the solution and fumed silica particles employed therein. The resulting catalyst particles contained 30 weight percent of thoria, calculated as $ThO_2$ and based on the total weight of the impregnated catalyst particles. A variety of aluminas (fumed, alpha, and gamma) were similarly tested and shown to be ineffective in the coupling reaction of the method of the invention.

EXAMPLE 10

50 grams of thorium nitrate ($Th(NO_3)_4 \cdot 4H_2O$) were calcined at 600° C. for 14 hours. The resulting Th(NO$_3$)$_4$·4H$_2$O, was sieved to isolate a 14/40-mesh fraction.

EXAMPLE 11-23

Each Examples 11-23 was performed using a simple quartz tube furnace reactor which had an inside diameter of 1.2 centimeters and was charged with 5 milliliters of 14/42-mesh catalysts which filled an 8-centimeter length of the reactor. The tube was then placed in a single zone 12-inch Lindberg furnace controlled by a Eurotherm 919 system. P-cresol was added at a general rate of 0.09-0.11 gram per minute using a Harvard Apparatus syringe drive P-cresol was dissolved in toluene at a mole ratio at 1:1 of toluene-to-p-cresol prior to addition. Generally, nitrogen at a 10 milliliter per minute flow rate was passed through the reactor and catalyst bed. Typically, the contact time of the feed compound and the catalyst bed was 3-4 seconds. Long term catalyst deactivation runs were performed in a similar fashion except that reactants were added at a constant controlled rate using a Constametice Model I pump. Components of the product mixture were identified by gas chromatography or gas chromatography-mass spectometry. Major products were separated by recrystallization or distillation.

The catalysts and conditions employed in Example 11-23 are indicated in Table 1, and the results from such examples are indicated in Table 2

TABLE 1

| Example | Catalyst from Example | % Loading | Wt. ThO$_2$ per Catalyst/Charge | Temperature (C.°) |
|---|---|---|---|---|
| 11 | 4 | 23 | 0.9 | 450 |
| 12 | 5 | 17 | 1.0 | 450 |
| 13 | 7 | 15 | 1.2 | 450 |
| 14 | 8 | 17 | 0.9 | 450 |
| 15 | 9 | 30 | 1.1 | 450 |
| 16 | 1 | 44 | 1.4 | 450 |
| 17 | 2 | 42 | 1.1 | 450 |
| 18 | 3 | 27 | 0.7 | 450 |
| 19 | 6 | 16 | 1.3 | 450 |
| 20 | 2 | 42 | 1.1 | 425 |
| 21 | 2 | 42 | 1.1 | 450 |
| 22 | 2 | 42 | 1.1 | 475 |
| 23 | 10 | 100 | 12.4 | 425 |

TABLE 2

| Example | % Conversion p-Cresol | Formation of % Yield | 4,4'-DMDPE % Selectivity |
|---|---|---|---|
| 11 | 5.0 | 3.0 | 60 |
| 12 | 20.0 | 15.5 | 77 |
| 13 | 18.8 | 0 | 0 |
| 14 | 2 | 1 | 50 |
| 15 | 56 | 3 | 5 |
| 16 | 30.7 | 27.8 | 90 |
| 17 | 34.5 | 27.8 | 80 |
| 18 | 19.1 | 18.0 | 94 |
| 19 | 18.9 | 17.5 | 92 |
| 20 | 18.0 | 14.4 | 80 |
| 21 | 34.5 | 27.8 | 80 |
| 22 | 53.3 | 39.7 | 74 |
| 23 | 41 | 38.9 | 95 |

Examples 11-15 and 23 and are comparative examples whole Examples 16-22 illustrate the method of this invention. Comparison of the results for Examples 16-22 with those of Examples 11-15 indicate that, in order to achieve the high selectivities for the formation of the desired product, 4,4'-dimethyldiphenyl ether, the method of this invention, it is essential to use a neutral substantially pure support. The use in Example 14 of the basic support, magnesium oxide, drastically inhibited the catalytic activity of the thorium oxide. The use in Examples 11-13 and 15 of the acidic supports resulted in increased amounts of isomerization, dealkylation, alkylation, and hence, reduced selectivities for the formation of the desired product.

From the above description, it is apparent that the objects of the present invention have been achieved. While only certain embodiments have been set forth, alternative embodiments and various modifications will be apparent from the above description to those skilled in the art. These alternatives are considered equivalents and within the spirit and scope of the present invention.

Having described the invention, what is claimed is:

1. A method for the formation of a diaryl ether or a diaryl sulfide comprising heating a phenol, a thiophenol, a β-hydroxy-substituted fused aromatic ring-system compound, or a β-thio-substituted fused aromatic ring-system compound in the gas phase at a temperature in the range of from about 300° C. to about 600° C. in the presence of a bed of catalyst particles comprising thorium oxide deposited on a support selected from the group consisting of pure silica, pure zirconia, carbon, asbestos and quartz.

2. The method of claim 1 comprising heating a phenol or a β-hydroxy-substituted fused aromatic ring-system compound to form a diaryl ether.

3. The method of claim 2 wherein the phenol or β-hydroxy substituted fused aromatic ring-system compound, apart from the phenolic oxygen substituent therein, either is otherwise unsubstituted or is substituted with either at least one alkyl group containing from 1 to 10 carbon atoms or at least one other substituent that is inert to the coupling reaction, or both, and wherein each aforesaid alkyl and other inert substituent is attached to an aromatic ring carbon atom that is located other than ortho to the phenolic oxygen substituent.

4. The method of claim 3 wherein the phenol or β-hydroxy-substituted fused aromatic ring-system compound is phenol, m-cresol, p-cresol, 3,4-xylenol, 3,5-xylenol, 3,4,5-trimethylphenol, 5-tetralinol.

5. The method of claim 2 wherein the phenol or β-hydroxy substituted fused aromatic ring-system compound is dissolved in a solvent that is inert to the formation of the ether or sulfide.

6. The method of claim 5 wherein the solvent comprises benzene, toluene, a xylene, a hexane, a heptane, tetrahydrofuran, or 1,4-dioxane.

7. The method of claim 2 wherein a carrier gas that is inert to the coupling reaction is employed to sweep the phenol or β-hydroxy-substituted fused aromatic ring-system compound through the catalyst bed.

8. The method of claim 7 wherein the carrier gas comprises hydrogen.

9. The method of claim 1 wherein the catalyst support is pure silica or pure zirconia and contains less then 1000 parts per million of metallic impurities calculated as the elemental metals.

10. The method of claim 9 wherein the catalyst support is fumed silica or zirconia.

11. The method of claim 2 wherein the catalyst is formed by calcination at a temperature in the range of from about 600° C. to about 800° C. of thorium salt deposited on the support.

12. The method of claim 11 wherein the support is calcined at 500°-1000° C. before deposition on it of the thorium salt.

13. The method of claim 2 wherein the reaction temperature is in the range of from about 425° C. to about 450° C.

14. The method of claim 13 wherein the reaction temperature is gradually increased at a rate of increase that is from about 0.04° C. to about 0.45° C. per day, within the temperature range of from about 425° C. to about 450° C.

* * * * *